Figure 1:
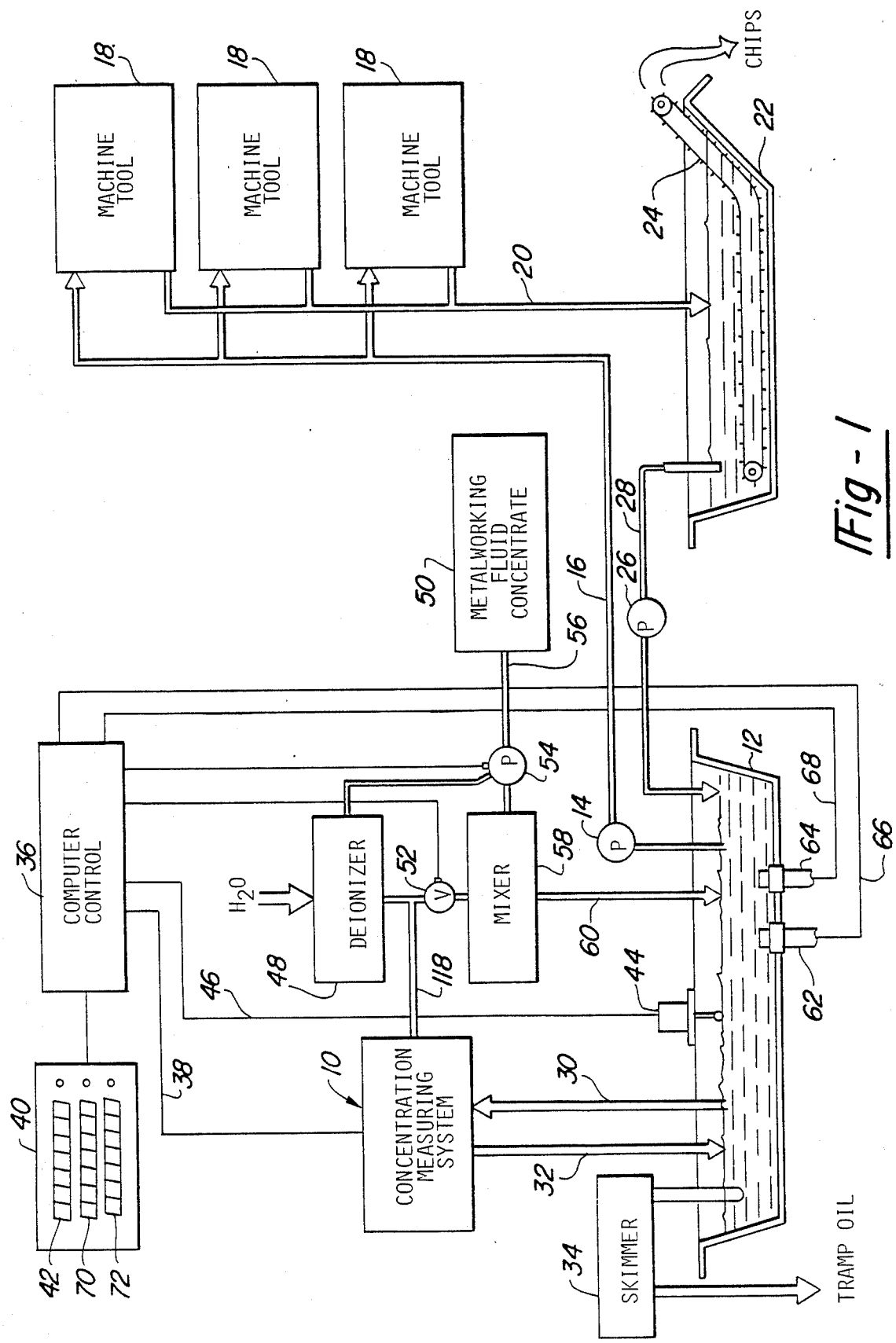

United States Patent [19]
Florig et al.

[11] Patent Number: 4,767,982
[45] Date of Patent: Aug. 30, 1988

[54] CONCENTRATION DETECTION SYSTEM

[75] Inventors: H. Keith Florig; David A. Purta, both of Pittsburgh, Pa.

[73] Assignee: Master Chemical Corporation, Perrysburg, Ohio

[21] Appl. No.: 56,543

[22] Filed: Jun. 1, 1987

[51] Int. Cl.[4] .......................................... G01R 27/04
[52] U.S. Cl. ............................. 324/58.5 A; 324/58 A
[58] Field of Search .......... 324/58.5 A, 58 A, 58.5 R, 324/58 R; 73/861.04

[56] References Cited

U.S. PATENT DOCUMENTS

| | | | |
|---|---|---|---|
| 2,966,057 | 12/1960 | Heller | 73/67.6 |
| 3,246,145 | 4/1966 | Higgins | 250/43.5 |
| 3,498,112 | 3/1970 | Howard | 73/61.1 |
| 3,851,244 | 11/1974 | Mounce | 324/58.5 A |
| 4,107,993 | 8/1978 | Shuff et al. | 324/58.5 R |
| 4,202,193 | 5/1980 | Wilson | 72/42 |
| 4,289,020 | 9/1981 | Paap | 73/61.1 |
| 4,301,400 | 11/1981 | Paap | 324/58.5 A |
| 4,429,273 | 1/1984 | Mazzagatti | 324/61 R |
| 4,484,133 | 11/1984 | Riggin | 324/58.5 A |
| 4,485,284 | 11/1984 | Pakulis | 324/58.5 A |
| 4,486,714 | 12/1984 | Davis, Jr. et al. | 324/58.5 A |
| 4,499,418 | 2/1985 | Helms | 324/58.5 A |
| 4,546,311 | 10/1985 | Knochel | 324/58.5 R |
| 4,620,146 | 10/1986 | Ishikawa et al. | 324/58.5 A |
| 4,651,085 | 3/1987 | Sakurai et al. | 324/58.5 R |

FOREIGN PATENT DOCUMENTS

| | | |
|---|---|---|
| 913181 | 10/1972 | Canada . |
| 1124959 | 8/1968 | United Kingdom ............ 73/61.1 R |
| 316967 | 12/1971 | U.S.S.R. . |

OTHER PUBLICATIONS

Y. Leviatan et al., "Analysis of Inductive Dielectric Posts in Rectangular Waveguide", IEEE Transactions on Microwave Theory & Techniques, vol. MTT-35, No. 1, Jan. 1987.

Primary Examiner—Reinhard J. Eisenzopf
Assistant Examiner—Anthony L. Miele
Attorney, Agent, or Firm—Irvin L. Groh; Alfred L. Patmore, Jr.; Freeman Crampton

[57] ABSTRACT

A system and method of measuring the concentration of each component of a two component liquid by passing a microwave signal through a flowing liquid sample. A waveguide is used between a microwave source and detector, and a sample tube passes through the central portion of the wave guide.

28 Claims, 2 Drawing Sheets

CONCENTRATION DETECTION SYSTEM

This invention relates to a method and apparatus for determining the concentration or proportion of each component of a two-component liquid. A two-component liquid is here defined as a solution, emulsion, or mixture of two substances which together form a liquid. Examples of two-component liquids include but are not limited to mixtures and emulsions of oil and water and solutions of salt in water.

Various techniques have been utilized for determining relative concentration in two-component liquids. These techniques have included chemical analysis and measurements of density, refractive index, sound velocity, infrared absorption, and dielectric properties. The present invention derives from the realization that measurements in the microwave region of the electromagnetic spectrum can offer a high degree of accuracy in measuring relative concentration in two-component liquids in cases where the microwave dielectric properties of the liquid are a strong function of relative concentration.

Microwave techniques that have been used in the past to infer concentration in liquids, have included measurements of the phase shift of a signal transmitted through or reflected from the sample liquid, measurements of the resonance properties of a cavity loaded with the sample liquid, or measurements of attenuation employing horn antennas. There are one or more drawbacks associated with each of these prior art microwave-based concentration detection systems. One significant drawback of all past systems is the high costs associated with microwave components such as isolators, directional couplers, tuners, variable attenuations, frequency meters, and klystrons. Another drawback is that most of these systems do not account for changes in the dielectric properties of the sample liquid caused by changes in sample temperature. A third disadvantage, common to some past devices, is susceptability to drifts in the power of the microwave generator and the efficiency of the microwave detector due either to aging or to changes in the temperature of the ambient air. A fourth problem, common to some devices, is that they require manual operation and interpretation and so are not suited for use in automated systems.

The principle objective of the current invention is an accurate system to measure relative concentration in two-component liquids by measuring the intensity of a microwave signal transmitted through the liquid. Another objective is to perform this function in an automated way with a minimum number of microwave components, and with provisions to adjust for both changes in the temperature of the liquid being measured and drifts in the performance of the microwave source and detector.

The present invention employs a longitudinally extending waveguide, preferrably with a rectangular cross-section. A transmitting source is located at one end for transmitting a microwave signal through the waveguide. A microwave detector is located at the other end of the waveguide for receiving the microwave signal. A sample tube, employing a material of low dielectric permittivity and loss, extends transversely through the broad face of the waveguide intermediate to its ends, and the liquid to be measured, the sample liquid, is caused to flow through the sample tube. The detector generates an electrical signal corresponding to the microwave signal that is received from the source through the waveguide, sample tube, and sample liquid. This signal is a function of the dielectric properties of the sample liquid, which, for the two-component liquids, is in turn a function of relative concentration. Signal processing circuitry and a digital microcomputer are connected to the microwave detector for computing the concentration of the material in the solution as a function of the electrical signal by comparing the signal with stored calibration information.

Since the detected microwave signal is generally a function of the temperature of the sample liquid as well as the concentration, in a preferred embodiment of the invention, the temperature is measured by means which provide an electrical signal as a function of the sample temperature, and this signal is provided to the signal processing circuitry and microcomputer for computing the relative concentration of the two-component liquid.

Both the power of the microwave source and the efficiency of the microwave detector can be affected by changes in ambient air temperature. In a preferred embodiment of the invention, the waveguide and its microwave source and microwave detector are contained in an enclosure in which a uniform temperature is maintained.

To eliminate the effects of drift which may be caused by aging of the microwave source or detector, or such things as deposits on the inside of the sample tube, valving and piping are arranged to provide means for interrupting the flow of the sample liquid through the sample tube and introducing a flow of a liquid sample of known concentration through the tube for recalibrating the circuit. For two-component liquids in which water is a primary component, pure or deionized water may be used as a sample liquid of known concentration.

In a preferred embodiment of the invention, the sample tube is surrounded and secured near the points of entrance to and exit from the waveguide by microwave shield tubes and appropriate fittings in such a way that the sample tube is surrounded by a metal collar for a distance of at least one-half of a wavelength beyond the surface of the waveguide. This arrests microwave leakage and assures that any mechanical relaxation in the fittings that secure the sample tube beyond the metal collar has a negligible effect on the impedance of the sample tube as seen by either the source or the detector.

There are several design variables that affect the sensitivity of the detector signal to changes in the concentration of the sample liquid. Among these variables are the microwave frequency at which the device operates, the diameter of the sample tube, and the longitudinal distances between the source and sample tube and between the sample tube and detector.

The frequency of the microwave source is selected to provide acceptable sensitivity for the liquid being measured in the concentration percentage range involved. For example, it is commonly known that the dielectric permittivity and the loss thereof in salt water is independent of salt concentration above 10–20 GHz. Applying the present invention to salt water solutions, requires the choice of a frequency well below this range. Applying the present invention to mixtures or emulsions of oil in water, may dictate the use of a frequency above this range so that device performance is not influenced by salt contaminants. Another factor to be considered in choosing a particular frequency is the commerical availability of microwave sources at that frequency.

The changes in microwave detector response with both fluid concentration and temperature has been found to be very sensitive to the diameter of the sample tube. The optimum sample tube diameter is one for which microwave detector response to changes in concentration is large and microwave detector response to changes in sample temperature is small. The sample tube diameter that maximizes the ratio of concentration sensitivity to temperature sensitivity can be determined either empirically or theoretically. If the dielectric permittivity and dielectric loss of the two-component sample liquid are known as a function of concentration and temperature, equivalent circuit models can be utilized such as those referenced and described in "Analysis of Inductive Dielectric Posts in Rectangular Waveguides", by Y. Leviatan and G. S. Sheaffer, IEEE Transactions on Microwave Theory and Techniques, Vol. MTT-35, No. 1, January 1987.

The theoretical modeling of detector response can be simplified if the source-to-sample and sample-to-detector distances are each chosen to be at least several guide wavelengths long. This assures that only the fundamental waveguide mode is propagated to the detector.

Another factor influencing the choice of source-to-sample and sample-to-detector distances is the multiple reflections that occur between components. By adjusting these distances to provide constructive interference of multiple reflections, the sensitivity of detector response to changes in concentration can be maximized. If maximum concentration sensitivity is found to occur at source-to-sample distance $D_1$ and sample-to-detector distance $D_2$ then, characteristic of standing wave phenonmenon, this same maximum will be found at separation distances that differ from $D_1$ and $D_2$ by multiples of one-quarter of a guide wavelength, provided the separations are at least two wavelengths long. In general, source-to-sample and sample-to-detector distances are chosen to maximize detector sensitivity to concentration within the ranges of concentration and temperature in which the system will operate.

Ultimately, the concentration level is displayed as by a LCD unit. In a commercial environment, the concentration of the liquid being measured can be automatically controlled from the measured signal and a desired set point by the addition of the appropriate component to the liquid.

The method of measuring the concentration of the liquid involves the following steps:
 establishing a flow of liquid to be measured;
 passing the liquid through a sample tube which extends transversely through a microwave guide;
 passing a microwave signal through from one end of the guide through the sample tube and the liquid flowing within it to the other end of the wave guide;
 detecting the strength of the microwave signal received at the other end of the wave guide and generating a microwave intensity electrical signal responsive thereto; and
 generating a liquid concentration signal from the microwave intensity signal.

In one preferred embodiment of the invention an additional step converts the liquid concentration signal to a visual display.

In another embodiment of the invention an additional step utilizes the liquid concentration signal to control the concentration of the liquid itself.

In another preferred embodiment of the invention the additional step of measuring the temperature of the liquid and generating an electrical signal which is a function of the temperature is included so that the generation of the liquid concentration signal combines both the temperature and microwave signals.

The method can also include the step of maintaining the measuring environment at a constant temperature and also the additional steps of interrupting the flow of liquid through the sample tube and flowing liquid of known concentration through the tube to produce a correcting signal to modify the liquid concentration signal.

Figure 2:
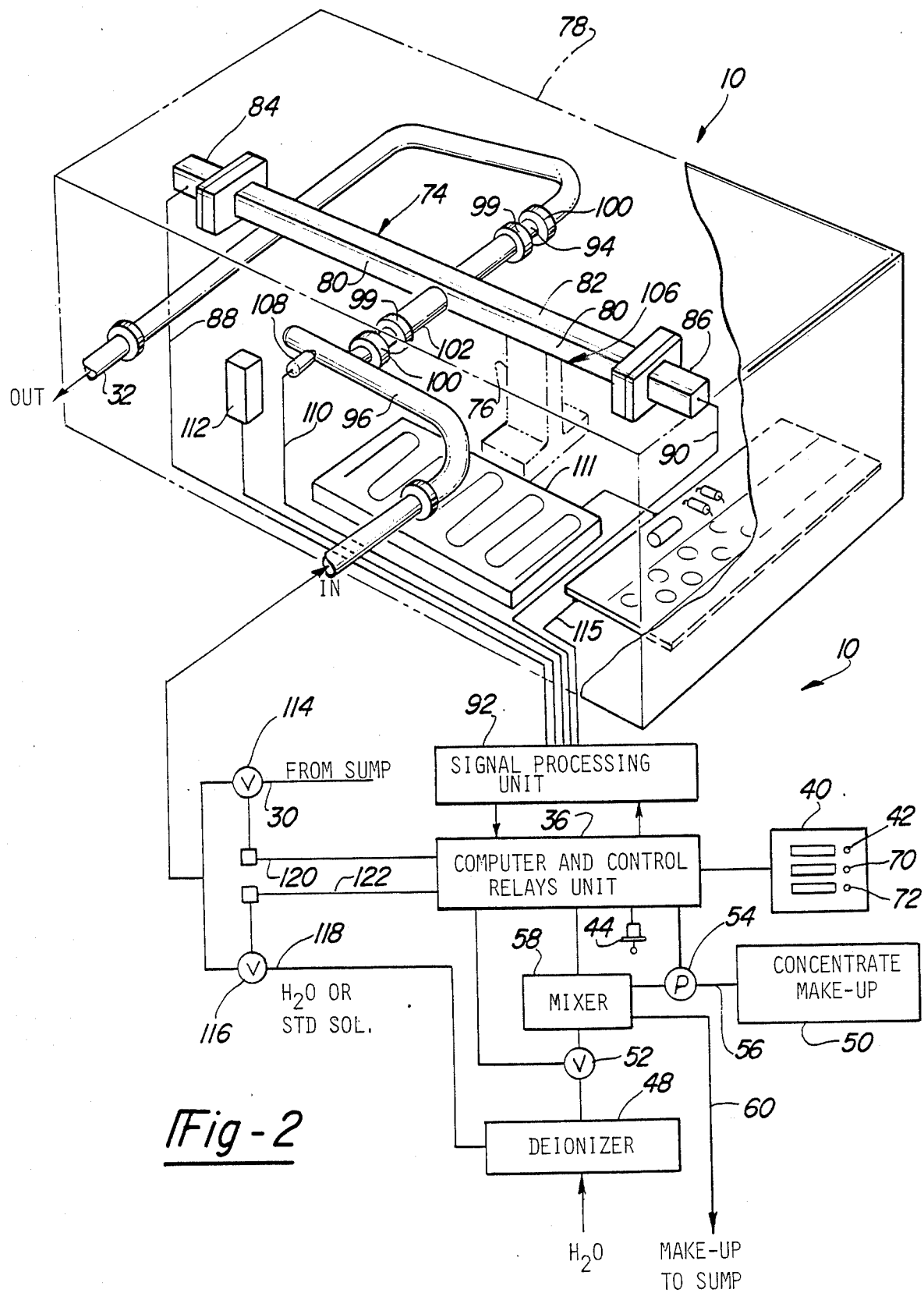

The invention is accomplished by the embodiments disclosed in the following description and illustrated in the drawing in which:

FIG. 1 is a diagrammatic view showing the concentration measuring system of this invention in an overall system for controlling concentration and cleanliness of metalworking or cutting fluid supplied to machine tools; and FIG. 2 is a diagrammatic view of the concentration measuring system of this invention.

Referring first to FIG. 1, the concentration measuring system 10 of this invention is employed in a system to maintain the proper concentration of a metalworking fluid which is supplied to a machine tool to provide both cooling of the working tool and proper lubricity between the tool and the metal stock used to form a final product. To supply the proper lubrication and cooling the metalworking fluid must have an effective wetting ability on the work and cutting tool.

Typically the metalworking fluid is a TRIM ® solution manufactured by Master Chemical Corporation which is supplied as a concentrated liquid and is mixed with water to provide a liquid with a nominal 10% concentration. A typical general use metalworking fluid such as TRIM ® SOL contains as its major ingredient a mineral oil along with minor amounts of substances such as a surfactant which aids in obtaining a finely dispersed emulsion with oil globule sizes of the order of one micron. In other special use metalworking fluids the major ingredient can be an organic salt, soap, surfactant, water soluble polymer, synthetic oil, alcohol, glycol or corrosion inhibitor.

It can thus be seen that in the metalworking fluid field the concentration measuring system must be adaptable to work with a wide range of materials. In this and other applications, such as determination of concentrations of salt, sugar and antifreeze in water, the system must also be readily adaptable for not only the material being detected, but also for the concentration range to be measured. For water-based metalworking fluids, for instance, the device must operate in a working range of 80–100% water.

In the machine tool environment as shown in FIG. 1, metalworking fluid is contained in sump 12 and is conveyed by pump 14 and line 16 to individual machine tools 18 where it performs the function of providing proper lubrication and cooling of the cutting tool and the work. In the process of providing cooling, some of the water content of the liquid is evaporated, and a portion of the liquid is retained on the work and the machine tool itself. Copious flow is used to each machine tool to flood the cutting tool and work not only for the lubrication and cooling effect that is accomplished but also to carry away the chips that are generated in the metal cutting process.

The used metalworking fluid is returned for reuse to the main sump 12. In some instances, the metal chips are allowed to collect in the individual machine tool sumps and are periodically removed therefrom. In larger installations the fluid is returned through a line 20 to a drag out tank 22 in which the chips are removed by an endless conveyor 24. Additional fluid is lost as it is carried away by the chips being removed from the drag out tank 22. The fluid is returned from the chip removal sump 22 to the main sump 12 by pump 26 and line 28. In some instances additional filtering may be introduced into the line 28.

As the fluid is used in the individual machine tools, it picks up a portion of the hydraulic fluid used to run the machine tool and the lubricating oil used to lubricate the various moving parts of the machine tool such as slides and spindles. This hydraulic fluid and lubricating oil is collectively known as tramp oil. The content of the tramp oil tends to increase as the fluid is recirculated in the system. This oil is immmiscable with the fluid itself and when its content exceeds 2%, it tends to form a film on the cutting tools and interfers with the cooling action of the fluid. Also such a high content of tramp oil in the fluid causes the chip particles to stick to the tools and a portion of the tramp oil will be vaporized during the machining operation producing an objectionable smoke or mist.

To eliminate the problems associated with the build up of tramp oil, a skimmer 34 such as the belt type "SCROUNGER ®" skimmer manufactured by Master Chemical Corporation is used to eliminate tramp oil from the sump 12. Alternatively, a centrifugal separator could be used.

Concentration of the fluid in the sump 12 is continuously monitored by concentration measuring system 10 which draws a continuous flow of fluid through pipe 30 and returns it to the sump 12 through pipe 32. The concentration level measured by system 10 is transmitted to control unit 36 by line 38 and may be displayed in digital form on instrument 40 by the LCD array 42. The control unit 36 can constitute a signal processing unit and a computer along with the necessary output relays.

As the metalworking fluid is consumed or dissipated by its use, the level of fluid in sump 12 drops and is detected by level controller 44 which sends a signal to control unit 36 through line 46. In order to maintain a fixed percentage of coolant or metalworking fluid in the system, it is necessary to add both water and metalworking fluid concentrate to the sump.

In order to use the system on a continuous basis, it has been found desirable to use deionized water to replace the water losses. The use of hard water would introduce corrosive salts, the concentrations of which would build up in the fluid as the water is evaporated. By utilizing a deionized water supply, calcium and magnesium ions are removed from the water supply so that the formation of insoluable calcium and magnesium salts are eliminated. Such other deleterious elements or compounds such as iron, carbonates, sulfates, nitrates, and chlorides are also removed in the deionizing process.

Pure, mineral-free water is supplied to the system by deionizer 48 which may be of the exchange tank deionizer type for smaller installations or of an automatic deionizer system for larger installations. Control 36 determines from the concentration measurement the proportion of deionized water to be introduced from deionizer 48 and the percentage of metalworking fluid concentrate to be introduced from sump 50. Appropriate control signals are issued from control unit 36 to water supply valve 52 and pump 54 in metalworking fluid concentrate line 56 which introduce the deionized water and metalworking fluid concentrate to mixer 58. A suitable mixer which is capable of handling a wide variety of concentrated liquids is the Unimix TM proportioner manufactured by Master Chemical Corporation. The properly mixed correct proportion of water and metalworking fluid concentrate is added to sump 12 from mixer 58 through line 60 to the desired level as determined by level controller 44.

In the overall control of the continuously operating metalworking fluid system, other properties which are secondary to the concentration level can be monitored. A pH detector 62 and conductivity detector 64 supply signals through respective lines 66 and 68 to control circuitry 36 for monitoring of these properties which can be displayed on LCD read outs 70 and 72 of instrument 40. To maintain product stability and inhibit corrosion, it is desirable to maintain the pH in the 7.5–10 range. The constant replenishing of the deionized water and metalworking fluid concentrate to the system will normally maintain such a pH level. However, minor additions of corrosion inhibitor, potassium hydroxide and water soluble amines may be made to maintain the proper pH.

Build up in the conductivity level would indicate a undesirable build up in dissolved salt level which could be created by contamination, the use of poor quality water or malfunction of the deionizer 48. Build up of dissolved salts may lead to corrosion, product instability, poor residues and increased bacterial growth.

For a water and metalworking fluid concentrate mixture which has heretofore been defined as a two-component liquid, the optimum microwave frequency for the concentration measuring system is somewhere in the neighborhood of 24 GHz. At this frequency, the absorption coefficient of water achieves a local maximum. Also at this frequency, the response of the sensor is insensitive to the build-up of salt concentration caused by evaporative losses of water from the fluid system. As mentioned previously, the dielectric permitivity and loss thereof in salt water is very nearly independent of salt concentration at frequencies above 20 GHz. Hence in one preferred embodiment of this invention, the source and detector are chosen to operate at 24.15 GHz, a frequency at which components are commercially available at low cost.

Referring to FIG. 2, the concentration measuring system 10 of this invention is shown in schematic form. A rectangular cross-section, elongate wave guide 74 is supported on pedestal 76 within heated enclosure 78. Waveguide 74 is EIA standard WR-42 brass waveguide with outside wider face 80 dimension of 0.5 inch and a narrower face 82 dimension of 0.25 inch. This waveguide will support fundamental mode transmission in the K-band between 18 GHz and 26.5 GHz.

The microwave source 84 in this embodiment is 24.15 GHz Gunn diode with a microwave output power of 10 milliwatts. The microwave source 84 is mounted at one end of the wave guide 74. The detecting elememt 86 is a medium barrier Schottky diode which is mounted at the other end of the wave guide 74. Suitable connections are made through wires 88 and 90 to signal processing unit 92 and the computer and control relay unit 36 to supply a regulated 4.5 volts to the microwave source 84 and for receiving and processing the signal from the detector 86.

A measuring or sample tube 94 in the form of a 2.0 inch length of 3.0 mm outside diameter by 1.8 mm inside diameter Pyrex tube passes through the broad face 80 of the wave guide at the center of its width and near the center of its length. Sample tube 94 is connected to conventional inlet tubing 96 and outlet tubing 98 by fittings 100 and is surrounded at its juncture to the wave guide by metallic microwave shield tubes 102 rigidly joined to waveguide 74. Fittings 99 are rigidly connected to shield tubes 102 and hold the sample tube 94 securely in place.

The wavelength at 24.15 GHz is 0.556 inches. To insure that only the fundamental mode impinges on the sample tube 94 and detector 86, the source-to-sample distance 104 and sample-to-detector distance 106 in this embodiment are made five guide wavelengths plus whatever increment of a wavelength leads to constructive interference of multiple reflections. As described previously, constructive interference of multiple reflections between the source and sample tube and between the sample tube and detector results in maximum sensitivity of the detector to changes in concentration. The lengths that yield constructive interference are determined empirically using waveguide shims. For this preferred embodiment, the first section 104 of the wave guide between the microwave source 84 and the sample tube 94 is 2.84 inches and the second section 106 of the waveguide 74 between the measuring tube 94 and the detector 86 is 3.25 inches.

The attenuation of the microwave signal from the source 84 to the detector 86 is created by passage through the liquid being sampled in sample tube 94 and is also dependent upon the temperature of that liquid. In a commercial environment, this temperature can be expected to vary over a given temperature range. To account for the effects of changes in sample temperature, the concentration sensing system is equipped with a temperature sensor 108 which transmits an analog temperatue signal to signal processing unit 92 and microcomputer 36 by conductor 110.

The relationship between concentration and the millivolt outputs of both the microwave detector and the temperature sensor is established experimentally and stored in the form of either a look-up table or a polynomial fit in microcomputer 36. The concentration of a sample is calculated by the microcomputer 36 by reading the microwave detector and temperature sensor and comparing those readings with the stored calibration information.

A source of error in a commercial environment is encountered when the temperatures of the source 84 and the detector 86 vary due to unpredictable changes in ambient air temperature. In order to eliminate this source of error, the entire sampling and measuring system has been incorporated into an enclosure 78 which is heated to a constant elevated temperature by panel heater 111 responsive to temperature detector 112 and performed by suitable heater circuitry on circuit board 92 through connections 113 and 115 with signal processing unit 92 and computer and control relay unit 36.

In order to compensate for aging of the microwave source and/or the detector and to account for other physical changes that could take place such as the accumulation of deposits on the inside of sample tube 94, the concentration measuring system 10 is originally calibrated with deionized water passing through the sample tube 94. The commercial installation is provided with means for interrupting the flow of liquid through the measuring tube and introducing a flow of deionized water through the measuring tube to obtain a recalibrating factor for the microwave measurement. This is accomplished by supplying a solenoid valve 114 in the line 30 from sump 12 and a solenoid valve 116 in a line 118 from deionizer 48 along with suitable control lines 120 and 122 respectively to the computer and control relay unit 36 performing this interruption on a periodic basis such as every six hours of operation.

The foregoing description has set forth the specific environment depicted in FIG. 1 of measuring the concentration of a metalworking fluid, and the use of a microwave signal at the higher end of the K-band has been utilized to show its suitability for detecting an oil in water mixture in the 0% to 20% oil range which is independent of dissolved salts. It is to be understood, however, that the detector as described and claimed is suitable for detecting the relative concentration in any two-component liquid provided the dielectric properties of the liquid change sufficiently with concentration in a frequency range in which a source and detector are commercially available. For example, this system has been utilized with a 10.525 GHz source and detector with a WR-90 wave guide, dimensioned for use in the X-band. The design parameters of the microwave concentration system have been set forth in such detail to permit the user to optimize the system for the particular liquid being sampled.

The embodiments of the invention in which an exclusive property or privilge is claimed are defined as follows:

1. A system for measuring the concentration of each component of a two component liquid comprising, in combination:
   a longitudinally extending metal microwave wave guide;
   a transmitting source located at one end of said wave guide for transmitting a microwave signal through said wave guide;
   a microwave detector located at the other end of said wave guide for receiving said microwave signal;
   a measuring tube extending transversely through said wave guide intermediate its ends;
   means for flowing said liquid through said measuring tube;
   said detector generating an electrical signal which is a function of the microwave signal received from said source through said wave guide, measuring tube and liquid;
   and computer means connected to said microwave detector for computing the concentration of each component in said liquid as a function of said electric signal.

2. The concentration measuring system according to claim 1 wherein the microwave source transmits a fixed frequency signal within the microwave spectrum.

3. The concentration measuring system according to claim 2 wherein said microwave source has a fixed frequency in the K-band whereby the measurement of the percentage of an oil in suspension forming an emulsion in water as the two component liquid can be readily detected independently of the amount of dissolved salts within the liquid.

4. The concentration measuring system according to claim 3 wherein said microwave source has a fixed frequency in the mid to upper K-band above approximately 20 GHz.

5. The concentration measuring system of claim 4 wherein the frequency of said source is 24.15 GHz.

6. The concentration measuring system of claim 3 wherein the component being measured is water and the percentage of oil in suspension is determined by subtracting the measured percentage of water detected from a nominal one hundred percent.

7. The concentration measuring system according to claim 2 wherein said wave guide has a rectangular cross-section with a larger width than height and said measuring tube extends centrally through said width.

8. The concentration measuring system according to claim 7 further including metal microwave shield tubes extending outwardly from said waveguide and surrounding said sample tube for a distance of at least one-half of a wavelength of said transmitted signal.

9. The concentration measuring system according to claim 8 wherein the measuring tube has a circular cross-section.

10. The concentration measuring system according to claim 1 wherein the wave guide has a first section between said microwave source and said measuring tube with a length which results in constructive interference of multiple reflections between the sample tube and the microwave source and said wave guide has a second section between said measuring tube and said detector with a length which results in constructive interference of multiple reflections between the sample tube and the microwave detector.

11. The concentration measuring system according to claim 1 wherein said microwave source transmits a fixed frequency signal within the microwave spectrum and the overall length of the wave guide is more then 4 times the wave length of the transmitted microwave signal.

12. The concentration measuring system of claim 1 further including means for measuring the temperature of said liquid upstream of said measuring tube and transmitting an electrical signal corresponding to said temperature to said computer means for computing the concentration of said material in said liquid.

13. The concentration measuring system of claim 1 further including a heated enclosure surrounding said wave guide, microwave source, microwave detector, and said measuring tube in order to maintain a uniform temperature thereof.

14. The concentration measuring system according to claim 1 further including means for interrupting the flow of liquid through said measuring tube, and means for introducing a flow of a fluid of known concentration through said measuring tube for recalibrating said circuit means responsive to the electrical signal generated during the passage of the fluid of known concentration through said measuring tube.

15. The concentration measuring system according to claim 9 wherein the means for introducing a flow of fluid of a known concentration through said measuring tube is connected to a source of deionized water to supply a fluid of known concentration.

16. The concentration system according to claim 1 further including means connected to said computer means for displaying the computed concentration of one of said components in said liquid.

17. The concentration measuring system according to claim 1 further including control means connected to said computer means for controlling the concentration of one of said components dissolved in said liquid responsive to the difference between a preselected concentration and the measured concentration.

18. The concentration measuring system of claim 1 wherein one of the components is water.

19. The concentration measuring system of claim 18 wherein the component being measured is water.

20. A system for measuring the concentration of each component of a two component liquid comprising, in combination;
a longitudinally extending metal microwave wave guide;
a transmitting source located at one end of said wave guide for transmitting a microwave signal through said wave guide;
a microwave detector located at the other end of said wave guide for receiving said microwave signal;
a measuring tube extending transversely through said wave guide intermediate its ends;
enclosure means surrounding said wave guide, microwave source, microwave detector and said measuring tube;
means for controlling the temperature within said enclosure;
means for flowing said liquid through said measuring tube;
means for measuring the temperature of said liquid and generating an electrical signal responsive thereto;
said detector generating an electrical signal which is a function of the microwave signal received from said source through said wave guide, measuring tube and liquid;
and circuit means connected to said microwave detector and said temperature detector for computing the concentration of each component in said liguid as a function of said electrical signals.

21. The concentration measuring system according to claim 17 further including valve means for interrupting the flow of liquid through said measuring tube and introducing a flow of water through said measuring tube for recalibrating said circuit means responsive to the electrical signal generated during the passage of water through said measuring tube.

22. A method of measuring concentration of a material in a liquid comprising the following steps:
establishing a flow of liquid to be measured;
passing the liquid through a measuring tube extending transversely through a microwave wave guide;
passing a microwave signal from one end of said wave guide through said measuring tube and said liquid flowing therein to the other end of said wave guide;
detecting the strength of said microwave signal received at the other end of said wave guide and generating a microwave intensity electrical signal responsive thereto; and
generating a liquid concentration signal from said microwave intensity signal.

23. The method according to claim 22 further including the step of converting said liquid concentration signal to a visual display.

24. The method according to claim 22 further including the step of controlling the concentration of said liquid responsive to said liquid concentration signal.

25. The method according to claim 22 further including the step of measuring the temperature of said liquid and generating an electrical signal which is a function of said temperature; and generating a liquid concentration signal from both said microwave intensity electrical signal and said temperature responsive signal.

26. The method of claim 25 further including the step of maintaining measuring environment at a constant temperature.

27. The method of claim 22 further including the following steps:
   interrupting the flow of liquid through said measuring tube;
   flowing a fluid of known concentration through said measuring tube;
   passing a microwave signal from one end of said wave guide through said measuring tube and the fluid of known concentration flowing therein to the other end of said a wave guide;
   detecting the microwave signal at the other end of said wave guide and generating a correcting, microwave intensity electrical signal responsive thereto; and
   modifying said liquid concentration signal with said correcting signal.

28. A system for measuring the concentration of each component in a two component liquid comprising, in combination:
   a longitudinally extending metal microwave wave guide having a rectangular cross-section with a larger width then height;
   a transmitting source located at one end of said wave guide for transmitting a fixed frequency microwave signal through said wave guide;
   a microwave detector located at the other end of said wave guide for receiving said microwave signal;
   a cylindrical measuring tube extending transversely through the width of said wave guide intermediate its ends;
   means for flowing said liquid through said measuring tube;
   means for measuring the temperature of said liquid and generating an electrical signal responsive thereto;
   said detector generating an electrical signal which is a function of the microwave signal received from said source through said wave guide, measuring tube and liquid;
   the diameter of said cylindrical measuring tube being selected to maximize the detector response to change in concentration of said liquid and to minimize the detector response to change in temperature of said liquid; and
   circuit means connected to said microwave detector and said temperature detector for computing the concentration of each component in said liquid as a function of said electrical signals.

* * * * *